United States Patent [19]

Moll

[11] Patent Number: 4,601,710

[45] Date of Patent: Jul. 22, 1986

[54] TROCAR ASSEMBLY

[75] Inventor: Frederic H. Moll, San Francisco, Calif.

[73] Assignee: Endotherapeutics Corporation, Redwood City, Calif.

[21] Appl. No.: 638,048

[22] Filed: Aug. 6, 1984

Related U.S. Application Data

[63] Continuation-in-part of Ser. No. 526,179, Aug. 24, 1983.

[51] Int. Cl.$^4$ ............................................. A61M 5/18
[52] U.S. Cl. .................... 604/165; 604/274; 128/305; 30/152; 30/162
[58] Field of Search .................... 604/158, 164–165, 604/169, 272–274; 128/305; 30/162, 151–152

[56] References Cited

U.S. PATENT DOCUMENTS

| 2,882,598 | 4/1959 | Fidelman | 30/162 |
|---|---|---|---|
| 4,091,537 | 5/1978 | Stevenson, Jr. | 30/151 |
| 4,230,123 | 10/1980 | Hawkins, Jr. | 604/165 |
| 4,393,587 | 7/1983 | Kloosterman | 30/162 |
| 4,414,974 | 11/1983 | Dotson et al. | 128/305 |
| 4,419,094 | 12/1983 | Patel | 604/158 |
| 4,447,236 | 5/1984 | Quinn | 604/169 |
| 4,473,076 | 9/1984 | Williams | 128/305 |
| 4,491,132 | 1/1985 | Aikins | 128/305 |
| 4,523,379 | 6/1985 | Osterhout et al. | 30/162 |
| 4,556,059 | 12/1985 | Adamson, Jr. | 604/157 |

Primary Examiner—Stephen C. Pellegrino
Assistant Examiner—Michelle Lester
Attorney, Agent, or Firm—Ciotti & Murashige

[57] ABSTRACT

A trocar assembly (70) formed from a trocar tube subassembly (74) and a separable, interfitting trocar subassembly (72). The trocar tube assembly includes a head (112) having a bore (120) into which a trocar tube (116) is fitted and a manually operated slide valve assembly (118) mounted transversely of the bore in the head. The valve has a bore (134) through it that may be aligned with the bore in the head by movement of the valve. The trocar subassembly includes a head (76) that has a bore (92) extending partly through it in which a trocar obturator (82) and a concentric tubular shield (86) are mounted such that the shield is capable of limited axial movement relative to the obturator between a normal, extended position in which the shield effectively covers the piercing tip (84) of the obturator and a retracted position in which the tip is exposed. The obturator and shield are inserted through the bore in the trocar tube subassembly head, the slide valve bore and the trocar tube. The bore in the slide valve has a radial tooth (136) in it that engages a slot (138) in the shield to reversibly lock the shield in its extended position when the slide valve is in its normal position. The valve is depressed manually to disengage the tooth to allow axial movement of the shield or separation of the trocar subassembly from the trocar tube subassembly.

4 Claims, 12 Drawing Figures

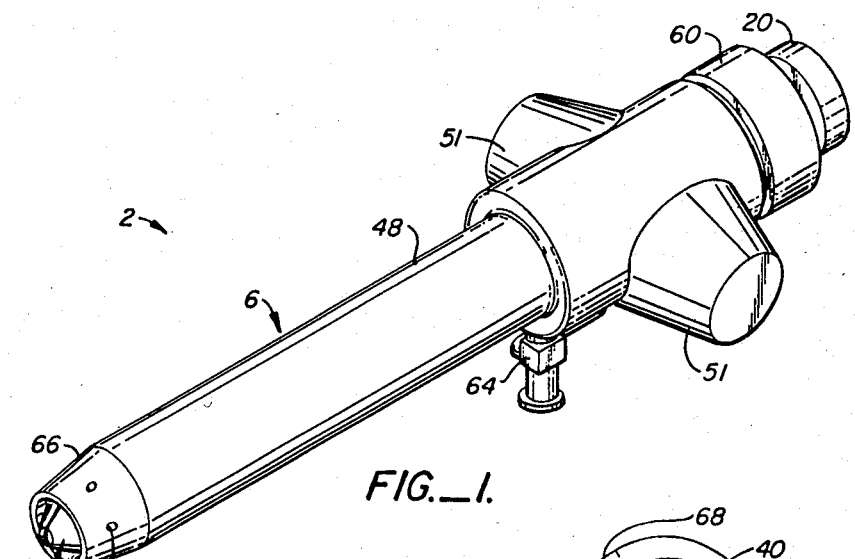
FIG._1.
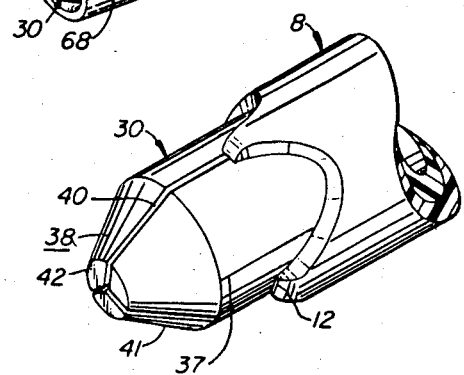
FIG._5A.
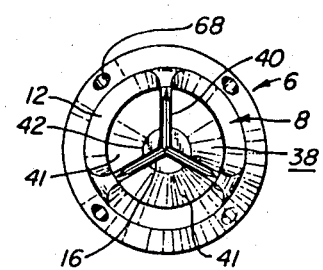
FIG._4.
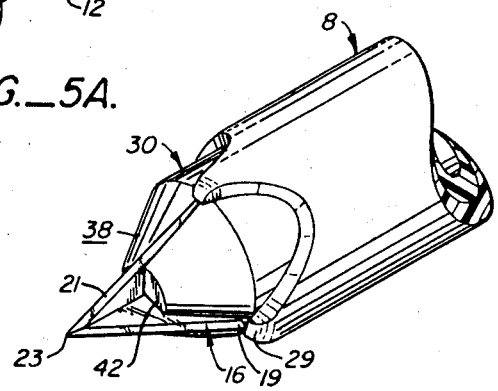
FIG._5B.

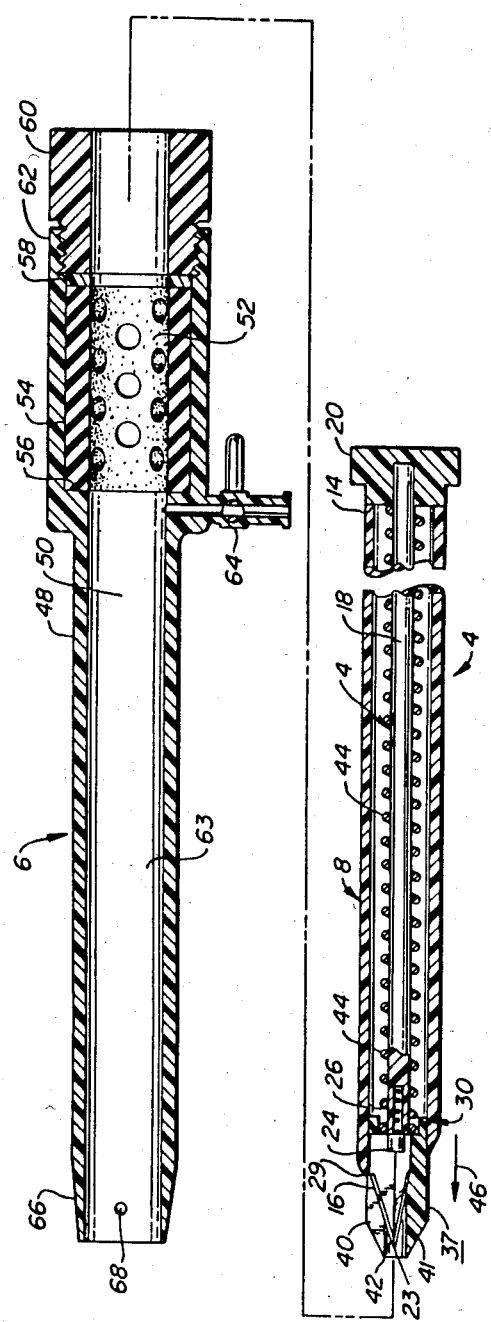
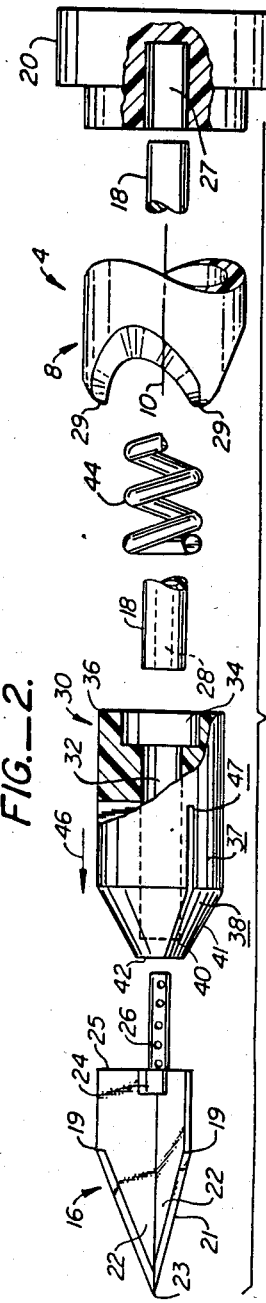
FIG._2.
FIG._3.

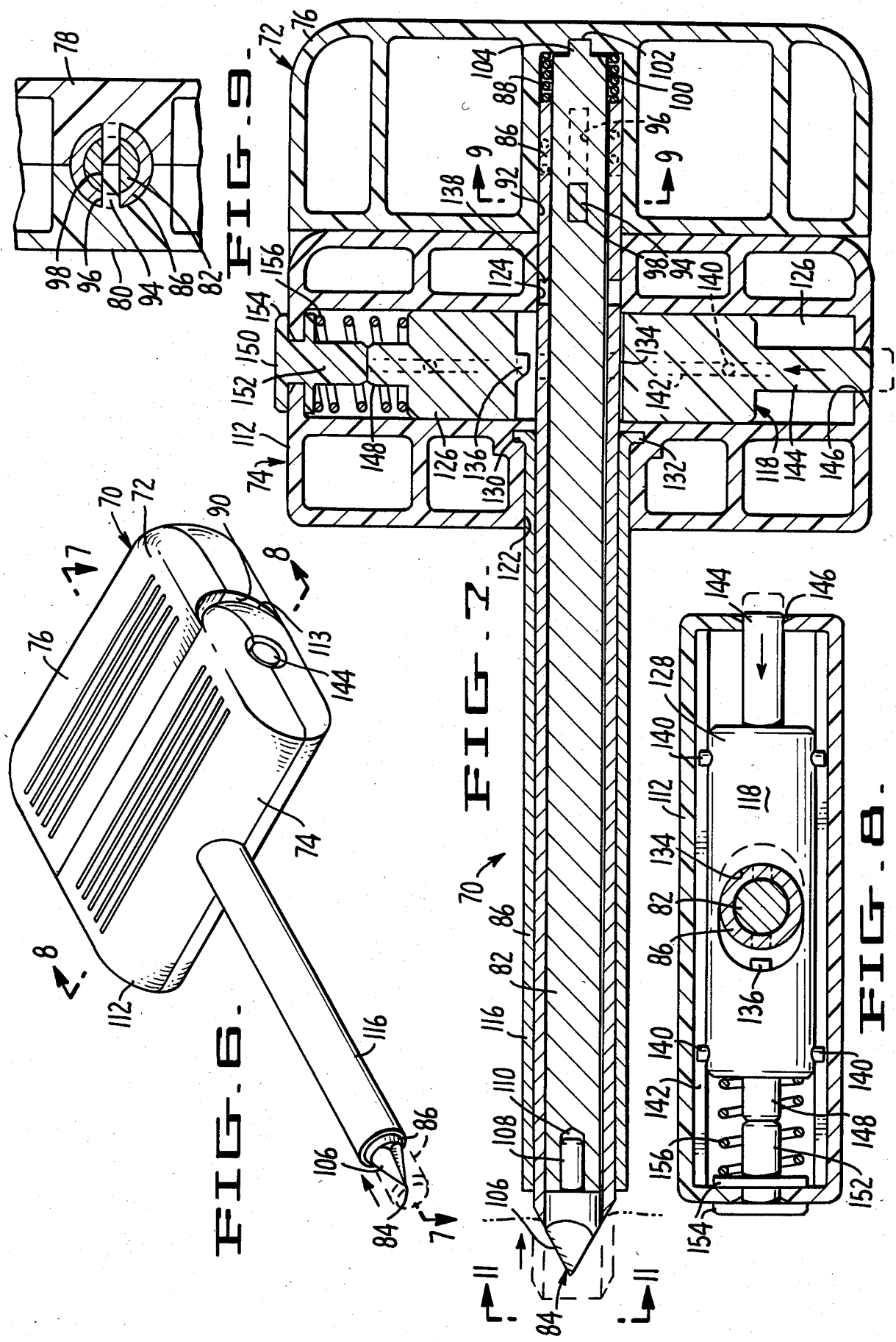

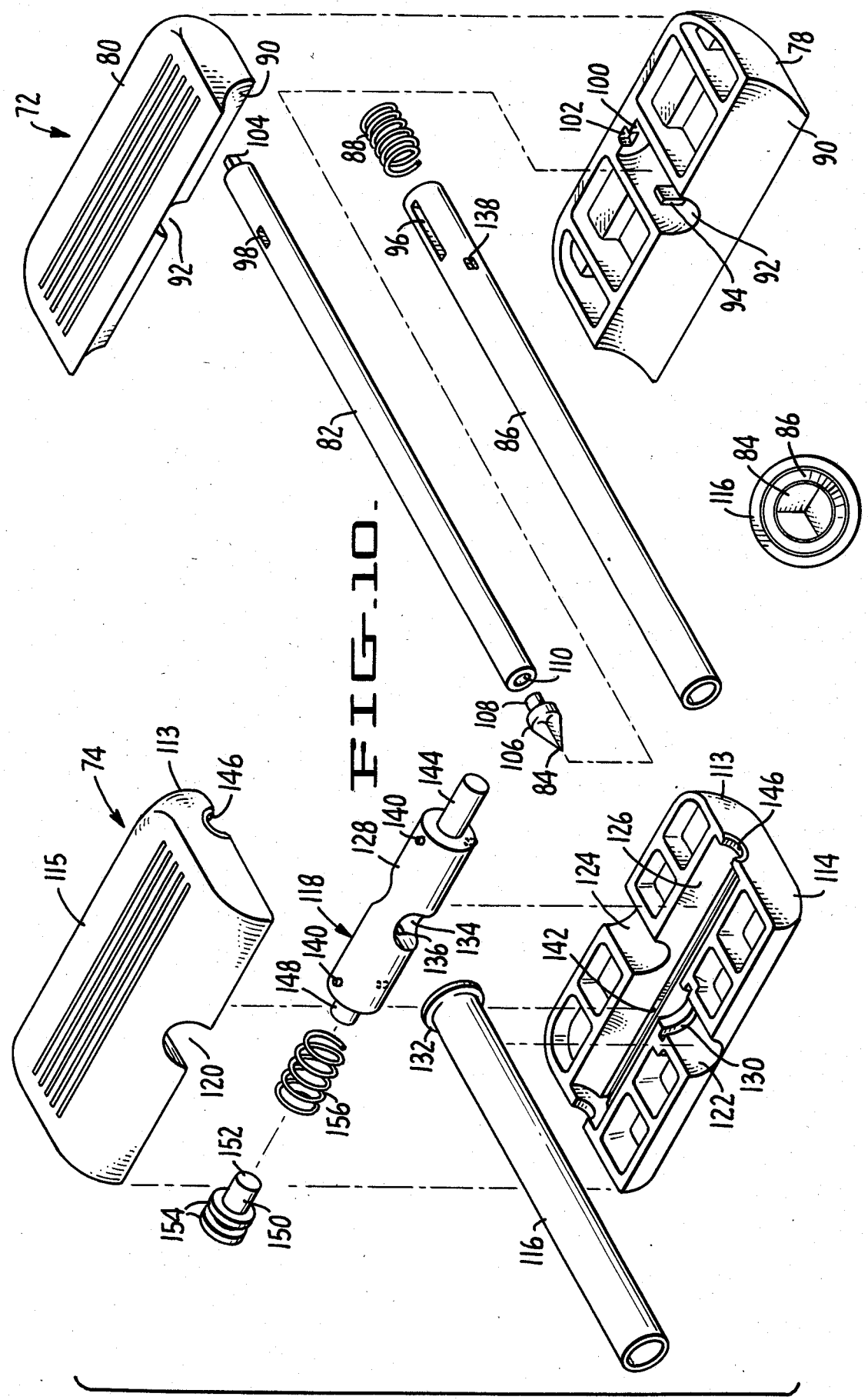

TROCAR ASSEMBLY

CROSS-REFERENCE TO RELATED APPLICAITON

This application is a continuation-in-part of copending U.S. patent application Ser. No. 526,179, filed Aug. 24 1983.

DESCRIPTION

1. Technical Field

The invention is in the field of surgical instruments. More particularly it concerns a novel trocar.

2. Background Art

Trocars are sharp pointed surgical instruments used to puncture a body cavity. This is often done so that fluids may be drained using a cannula inserted into the opening. Trocars are also used during endoscopic procedures. A conventional endoscopic procedure follows three steps. The first step is the insertion of a Veress cannula into the abdominal cavity through a small incision in the abdominal wall. The Veress cannula includes a hollow needle having a sharp point with an inside diameter of approximately 0.5 mm. When the cavity is entered, a spring-loaded pin inside the lumen of the needle pops out to extend a short distance, typically 1 mm, beyond the needle's point. This protects against inadvertent laceration of intra-abdominal structures. Because the pin is spring-loaded, it is not able to protrude beyond the needle's point until the abdominal cavity is entered. Next, the abdominal cavity is inflated with a gas through a small lumen in the Veress cannula. After inflation, the Veress cannula is removed. Finally, a standard trocar housed within the bore of a trocar tube is thrust into the inflated abdomen. Standard trocars are shaped like a large metal peg with a sharpened point, having a diameter varying from 3-12 mm. The trocar is then removed and the endoscopic instrument is inserted into the abdominal cavity through the trocar tube.

A major problem with existing trocars is that the sharpened tip of the trocar, after being thrust through the abdominal wall, can inadvertently puncture or lacerate intra-abdominal tissue. Also, conventional trocars are generally not disposable.

DISCLOSURE OF THE INVENTION

The present invention relates to a trocar assembly that is lightweight, easy to use, disposable if desired, and much safer to use than previous trocars.

The trocar assembly of the invention comprises:

(a) an elongate trocar obturator having a piercing tip at its front end;

(b) an elongate trocar tube in which the trocar obturator is housed;

(c) a tubular protective shield mounted concentrically around the trocar obturator and being axially movable relative to the trocar obturator between a normally extended position and a retracted position; and (d) biasing means acting on the rear end of the protective shield, whereby the shield is forced to said retracted position to expose the piercing tip when the trocar is being inserted through the wall of a body cavity and is biased by said means to said extended position to shield the piercing tip once the trocar has pierced the wall.

BRIEF DESCRIPTION OF THE DRAWINGS

FIG. 1 is an isometric view of one embodiment of the trocar assembly of the present invention.

FIG. 2 is a cross-sectional view of the trocar and trocar tube of FIG. 1.

FIG. 3 is an enlarged, exploded view of the trocar of FIG. 2.

FIG. 4 is a front end view of the trocar assembly of FIG. 1.

FIGS. 5A and 5B are isometric views of the trocar of FIG. 2 with the shield in extended and retracted positions.

FIG. 6 is an isometric view of an alternative, preferred embodiment of the trocar assembly of the invention.

FIG. 7 is a sectional plan view of the trocar of FIG. 6 taken along line 7—7.

FIG. 8 is a sectional view of the trocar of FIG. 6 taken along line 8—8.

FIG. 9 is a partial sectional view of the trocar of FIG. 6 taken along line 9—9.

FIG. 10 is an exploded view of the trocar of FIG. 6.

FIG. 11 is an end view of the piercing tip of the trocar of FIG. 6.

MODES FOR CARRYING OUT THE INVENTION

FIGS. 1 through 5 depict a trocar assembly, generally designated 2, that includes a trocar 4 and a trocar tube 6.

Trocar 4, shown best in FIGS. 2 and 3, includes an elongate tubular body 8 having a central axis 10 and open front and rear ends 12, 14. A piercing tip 16 is mounted to front end 12 of body 8 by an elongate shaft 18 extending along central axis 10 between tip 16 and end cap 20.

Piercing tip 16 includes three blades 22 extending from a central portion 24 between a common point 23 and a shoulder 25. Each blade 22 has a cutting edge 21 extending between common tip 23 and an outer end 19. Portion 24 includes a rearwardly extending peg 26 sized to fit within a bore 28 within one end of shaft 18. Peg 28 is fixed within bore 28 and the other end of shaft 18 is fixed within a bore 27 in cap 20 using a suitable adhesive. Shaft 18 is sized so the outer ends 19 of cutting edges 21 are generally aligned with leading surfaces 29 at front end 12 of body 8. Tip 16 does not move relative to body 8.

Piercing tip 16 may be stainless steel or of some other suitable material. If trocar 4 is to be a single use, disposable instrument, piercing tip 16 may be made from metal, hard plastic or some other material suitable for single use applications.

Housed within body 8 and surrounding tip 16 is a protective shield 30. Shield 30 is a generally cylindrical tubular member having a central bore 32 with an enlarged region 34 at the rear end 36 of shield 30. Shield 30 includes a cylindrical outer surface 37 sized for sliding movement along central axis 10 within body 8 and a forward and inwardly tapering conical outer surface 38. Three radially extending slots 40 are formed through protective shield 30 and extend from the front end 42 of shield 30 to a position medially along the protective shield. Slots 40 define three fingers 41 so that blades 22 are housed within slots 40 and between fingers 41; central portion 24 is housed within central bore 32. To mount shield 30 over tip 16, fingers 41 are separated at front end 42 and peg 26 and central portion 24 are inserted past front end 42 and into bore 32.

A spring 44 is captured between end cap 20 and enlarged region 34 to bias shield 30 forward in the direction of arrow 46 towards front end 12 of tubular body 8 so that fingers 41 normally cover or shield blades 22 of piercing tip 16. This position is shown in FIGS. 1, 2 and 5A. Such forward movement is halted when the bases 47 of slots 40 engage shoulders 25 of blades 22. During use, as described below, protective shield 30 is pushed rearwardly away from point 23 of tip 16 thus exposing tip 16 as shown in FIG. 5B.

Trocar tube 6, shown in FIGS. 1 and 2, is used in a conventional manner to guide trocar 4 in piercing the abdominal wall of the patient and also for later guiding a medical instrument, such as an endoscopic instrument (for exploration of the body cavity) or a cannula (for draining fluids from the body cavity). Trocar tube 6 inclues a generally tubular body 48 defining a central bore 50. A pair of gripping lugs 51 extend from body 48. Bore 50 is sized for axial sliding movement of trocar 4 therein.

Bore 50 includes an enlarged rear region 52 which houses a somewhat spongy cylindrical seal 54. Seal 54 is captured between a shoulder 56 in body 48 and a washer 58. Washer 58 is pressed against seal 54 by a cylindrical threaded sleeve 60 threadably mounted to the rear end 62 of body 48. As shown in FIG. 2, the inside diameter of seal 54 is normally about the same as that of the main portion 63 of central bore 50. Tightening threaded sleeve 60 against washer 58 compresses cylindrical seal 54 axially to deform the seal radially inwardly against the outer surface of the trocar 4 or other device housed therein.

Body 48 includes a valve 64 fluidly communicating with main region 63 of central bore 50. Cylindrical seal 54 insures that when a pressurized gas is pumped into central bore 50 through valve 64, or when a partial vacuum drawn on central bore 50 through valve 64, seal 54 blocks the potential flow path through region 52.

In use, trocar 4 is inserted into trocar tube 6. However, threaded cap 60 is not tightened down to allow trocar 4 to slide easily within trocar tube 6. After the patient's abdomen has been properly inflated with a gas, as described in the Background Art section, trocar 4, guided by tube 6, is used to pierce the patient's abdominal wall. Because of the substantial resistance of the abdominal wall, protective shield 30 is pushed rearwardly to allow piercing tip 16 to pierce and pass through the abdominal wall. Once piercing tip 16 has passed through the abdominal wall and enters the abdominal cavity, spring 44 biases protective shield 30 forward in the direction of arrow 46 to cover blades 22; this helps protect against any inadvertent puncturing or laceration of intra-abdominal tissues. If desired trocar 4 can be partially withdrawn from tube 6, sleeve 60 tightened and a gas introduced into the patient's abdominal cavity through valve 64. Seal 54 both secures trocar 4 in place and prevents gas from leaking past it.

During, for example, an endoscopic examination, trocar 4 is withdrawn from tube 6 and an endoscopic instrument (not shown) is inserted into the abdominal cavity of the patient through trocar tube 6. To keep the abdomen inflated, a gas can be slowly forced into the abdomen through valve 64. The gas passes along central bore 50 between tubular body 48 and the endoscopic instrument and finally into the abdominal cavity through holes 68 formed within tube 48 at front end 66 of tube 6. To keep the gas from escaping past region 52, threaded cap 60 is tightened onto washer 58 to squeeze cylindrical seal 54 between the interior wall of tubular body 48 bounding region 52 and the outside surface of the endoscopic instrument. This also helps to keep the medical instrument in place.

FIGS. 6 through 11 depict an alternate trocar assembly, generally designated 70, composed of a trocar subassembly 72 and a trocar tube subassembly 74. The two subassemblies are interfitting, but designed to be separable from each other. Referring to FIGS. 7 and 10, the basic elements of trocar subassembly 72 are a head or grip 76 composed of identical halves 78, 80 that are held together by fastening means such as snaps, adhesive, welds, or screws (not shown); an obturator 82 having a piercing tip 84; a tubular obturator sleeve or shield 86, and a spring 88 for biasing the shield. Grip 76 has a concave front wall 90 a central cylindrical bore 92 that extends from the wall 90 partly through the grip. The cylindrical wall of bore 92 carries a pair of mating, diametrically opposed posts 94 (one in each grip half) that are received through axial slots 96 and 98 in the shield 86 and obturator 82, respectively, for locking the obturator and shield in the subassembly. The end wall 100 of bore 92 has a generally cubic slot 102 that receives a cubic key or pin 104 on the rear end of obturator 82 for preventing rotation of the obturator. Helical spring 88 fits around the rear end of the obturator with its ends seated against wall 100 and the rear end wall of tubular shield 86. As described in detail below the spring biases the sheath forwardly to an extended position. In this regard slot 96 in the shield is elongated axially to permit limited axial movement of the shield relative to the obturator.

The piercing tip 84 has a pointed head 106 that serves to pierce through the wall of the body cavity and a cylindrical shank 108 that fits into a bore 110 in the front end of the obturator. The shank may be fixed in the bore or be mounted removably therein by means of threads or set screws. Removable mounting allows the tip to be removed for sharpening or cleaning or be replaced, if desired. The pointed end of the head is defined by three flat surfaces (FIG. 11) that form a pyramid. Alternatively the head may be conical in shape.

The principal elements of trocar tube subassembly 74 are: a head or grip 112 composed of two identical halves 114, 115 that are held together by fastening means (not shown); a trocar tube 116 and a slide valve assembly, generally designated 118. The rear wall of grip 112 has a convex shape that mates with the concavity of the front wall of the grip of the trocar subassembly so that the two subassemblies fit together snugly (FIGS. 6 and 7). As shown in FIG. 10, the grip has a central cylindrical bore 120 that extends through the grip from its front wall to its end wall. It is composed of a front section 122 that receives the trocar tube 116 and a rear section 124 that receives the obturator/shield of the trocar subassembly. It is traversed by a cylindrical cavity 126 that is adapted to receive body 128 of the slide valve. Front section 122 has a circumferential slot 130 in it that receives a circumferential collar or flange 132 formed on the rear end of trocar tube 116, whereby the axial position of the tube in section 122 is fixed.

The body of the slide valve has a central diametrical bore 134 that is adapted to receive the obturator/shield of the trocar subassembly. The bore has a radial locking tooth 136 that is adapted to engage a valve locking slot 138 in the side of the trocar shield 86 during operation of the trocar. The top and bottom (as shown in the Figures) of the cylindrical exterior of the body carries pairs of spaced, axially aligned guide posts 140 that fit, respectively, in axial slots 142 formed in the bottoms of the semicylindrical recesses in the grip halves that define cavity 126 to prevent rotation of the valve body. One end of the valve body carries a cylindrical shaft 144 that is received through an opening 146 in one sidewall of the grip. The shaft serves to support the body and as a point of manual contact for sliding the valve axially within cavity 126. The other end of the valve body has a cylindrical extension 148 that serves in combination with stop 150 to limit the axial movement of the valve in the cavity. Stop 150 has a cylindrical body 152 that aligns axially with extension 148 and a head defined by a pair of axially spaced circumferential collars 154 one of which abuts one end wall of the cavity 126 and the other of which abuts the exterior surface of the grip end wall. A coil spring 156 is received around extension 148 and stop body 152 with its ends seated, respectively, against the inner surface of the inner stop collar 154 and one end of the valve body. Spring 156 serves to bias the valve body axially.

The trocar of FIGS. 6-11 operates and is used as follows. Before use the trocar will be in the assembled form shown in FIGS. 6 and 7 with the two subassembly grips fitting snugly together and the trocar obturator and shield inserted through bore 120 in the trocar tube grip, bore 134 through the valve body, and the lumen of the trocar tube. The trocar shield is normally in a locked, extended forward position (shown in phantom in FIG. 7) due to the force exerted by spring 88 with locking tooth 136 of the valve engaged in the locking slot in the trocar shield. In this position the piercing tip is shielded from damage or contamination.

The trocar assembly is held by means of the interfitting grips of the two subassemblies and the shielded, leading end of trocar is placed against the skin that defines the outer surface of the wall of the cavity to be pierced. The slide valve 118 is then depressed (to the position shown in phantom in FIG. 8) by pressing on the exposed end of shaft 144. This action moves the valve body toward the valve stop and disengages tooth 136 from its locking slot, thereby permitting axial movement of the shield. Exertion of pressure against the skin with the trocar causes the shield to be pushed rearwardly against the spring to a retracted position (shown on solid line in FIG. 7) to expose the piercing tip of the trocar. The tip penetrates the skin and underlying tissue with continued pressure. Pressure on the end of shaft 144 is released shortly after the tip begins penetrating the wall (i.e., after the locking slot has moved rearwardly of the locking tooth position). Once the tip has penetrated through the wall and has entered the cavity the force against the front end of the shield ceases and the shield is automatically moved axially back to its extended, locked position through the action of spring 88. Viscera and other internal tissues are thus protected from contact with the sharp piercing tip and potential damage therefrom.

Once the cavity wall has been penetrated completely by the leading end of the trocar subassembly the slide valve can be re-depressed to disengage the locking tooth and the obturator/shield removed from the trocar tube by separating the trocar subassembly from the trocar tube subassembly. This separation leaves an open channel defined by the bores 120 and 134 and the lumen of the trocar tube to the body cavity through which surgical instruments may be placed to view internal tissues, perform operations thereon, or drain body fluids. The slide valve 118 may, if desired, be designed to move axially to a position in which its bore does not align with section 122 to block the channel when the trocar subassembly is withdrawn.

The trocar subassembly may, if necessary or desirable, be equipped with sealing means similar to that shown in the trocar of FIGS. 1-5 or seals conventionally used in medical instruments. The slide valve assembly may also be equipped with seals if necessary or desirable.

Modifications of the above described modes of carrying out the invention that are obvious to those of skill in mechanical engineering, surgical instrument design, or related fields are intended to be within the scope of the following claims.

I claim:
1. A trocar assembly comprising:
   (a) an elongate trocar obturator having a piercing tip at its front end;
   (b) and an elongate trocar tube in which the trocar obturator is housed;
   (c) a tubular protective shield mounted concentrically around the trocar obturator and being axially movable relative to the trocar obturator between a normally extended position and a retracted position; and
   (d) biasing means acting on the rear end of the protective shield, whereby the shield is forced to said retracted position to expose the piercing tip when the trocar is being inserted through the wall of a body cavity and is biased by said means to said extended position to shield the piercing tip once the trocar has pierced the wall.
2. The trocar assembly of claim 1 wherein the assembly includes:
   (e) means for reversibly locking the shield in said extended position.
3. The trocar assembly of claim 2 wherein the means for reversibly locking the shield in said extended position is a manually operable slide valve that has a bore through which the obturator and shield extend, the bore has a radial locking tooth that is adapted to engage a slot in the wall of the shield, the valve being slidable transversely to the shield from a normally locked position in which the tooth is engaged in the slot to an unlocked position in which the tooth is disengaged, whereby the shield may be moved axially to said retracted position.
4. The trocar assembly of claim 1, wherein the assembly includes:
   (e) means for limiting the axial movement of the shield relative to the obturator to positions between the extended position and retracted position.

* * * * *

UNITED STATES PATENT AND TRADEMARK OFFICE
CERTIFICATE OF CORRECTION

PATENT NO. : B1 4,601,710
DATED : May 5, 1998
INVENTOR(S) : Frederic H. Moll

It is certified that error appears in the above-identified patent and that said Letters Patent is hereby corrected as shown below:

On the title page, item [73]:

lange the Assignee from Endotherapeutics to United States Surgical Corporation.

Signed and Sealed this

Twenty-third Day of March, 1999

Attest:

Q. TODD DICKINSON

Attesting Officer     Acting Commissioner of Patents and Trademarks

REEXAMINATION CERTIFICATE (3503rd)

United States Patent [19]
Moll

[11] B1 4,601,710
[45] Certificate Issued May 5, 1998

[54] TROCAR ASSEMBLY

[75] Inventor: Frederic H. Moll, San Francisco, Calif.

[73] Assignee: Endotherapeutics Corporation, Norwalk, Conn.

Reexamination Request:
No. 90/004,129, Feb. 1, 1996

Reexamination Certificate for:
Patent No.: 4,601,710
Issued: Jul. 22, 1986
Appl. No.: 638,048
Filed: Aug. 6, 1984

Related U.S. Application Data

[63] Continuation-in-part of Ser. No. 526,179, Aug. 24, 1983.

[51] Int. Cl.$^6$ ..................................... A61M 5/18
[52] U.S. Cl. .................. 604/165; 604/274; 604/164
[58] Field of Search .......................... 128/749, 751, 128/753, 754; 604/158, 164, 165, 169, 272, 273, 274

[56] References Cited

U.S. PATENT DOCUMENTS

| | | | |
|---|---|---|---|
| 854,956 | 5/1907 | Martin . | |
| 1,147,408 | 7/1915 | Kells . | |
| 1,213,001 | 1/1917 | Philips . | |
| 2,882,598 | 4/1959 | Fidelman | 30/162 |
| 3,547,119 | 12/1970 | Hall et al. | 604/164 |
| 4,000,739 | 1/1977 | Stevens | 604/169 |
| 4,091,537 | 5/1978 | Stevenson, Jr. | 30/151 |
| 4,139,011 | 2/1979 | Benoit et al. . | |
| 4,230,123 | 10/1980 | Hawkins, Jr. | 604/165 |
| 4,254,762 | 3/1981 | Yoon . | |
| 4,393,587 | 7/1983 | Kloosterman | 30/162 |
| 4,414,974 | 11/1983 | Dotson et al. | 128/305 |
| 4,419,094 | 12/1983 | Patel | 604/158 |
| 4,447,236 | 5/1984 | Quinn | 604/169 |
| 4,473,076 | 9/1984 | Williams | 128/305 |
| 4,491,132 | 1/1985 | Aikins | 128/305 |
| 4,523,379 | 6/1985 | Osterhout et al. | 30/162 |
| 4,535,773 | 8/1985 | Yoon . | |
| 4,556,059 | 12/1985 | Adamson, Jr. | 604/157 |

FOREIGN PATENT DOCUMENTS

| | | |
|---|---|---|
| 836392 | 4/1952 | Germany . |
| 475215 | 10/1952 | Italy . |
| 921554 | 4/1982 | U.S.S.R. . |
| 1356386 | 6/1974 | United Kingdom . |

OTHER PUBLICATIONS

Subairov, Needle For the Puncture and Lavage of the Abdominal Cavity, "Surgery" Journal, 1976.
Markelov, "Trocar," Jan. 1981 with English translation.

*Primary Examiner*—Sam Rimell

[57] ABSTRACT

A trocar assembly (70) formed from a trocar tube subassembly (74) and a separable, interfitting trocar subassembly (72). The trocar tube assembly includes a head (112) having a bore (120) into which a trocar tube (116) is fitted and a manually operated slide valve assembly (118) mounted transversely of the bore in the head. The valve has a bore (134) through it that may be aligned with the bore in the head by movement of the valve. The trocar subassembly includes a head (76) that has a bore (92) extending partly through it in which a trocar obturator (82) and a concentric tubular shield (86) are mounted such that the shield is capable of limited axial movement relative to the obturator between a normal, extended position in which the shield effectively covers the piercing tip (84) of the obturator and a retracted position in which the tip is exposed. The obturator and shield are inserted through the bore in the trocar tube subassembly head, the slide valve bore and the trocar tube. The bore in the slide valve has a radial tooth (136) in it that engages a slot (138) in the shield to reversibly lock the shield in its extended position when the slide valve is in its normal position. The valve is depressed manually to disengage the tooth to allow axial movement of the shield or separation of the trocar subassembly from the trocar tube subassembly.

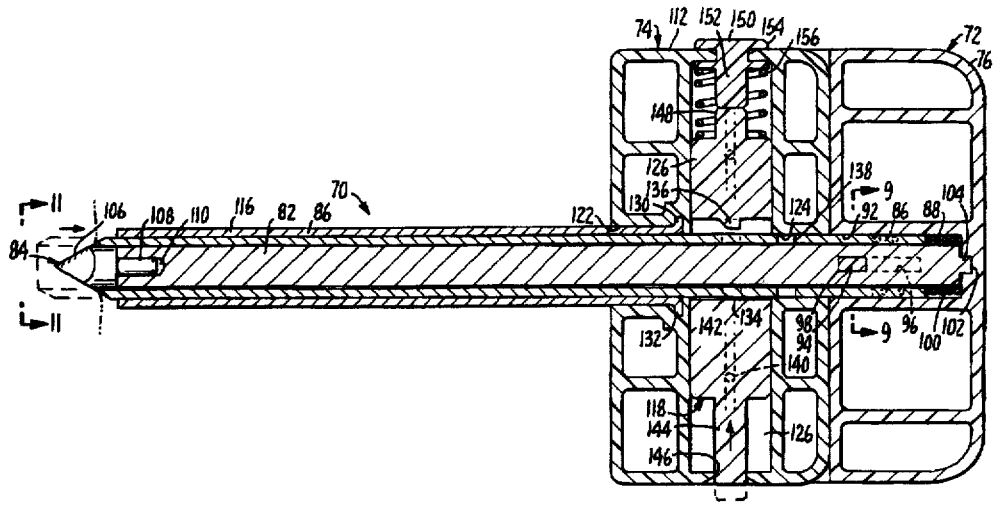

B1 4,601,710

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2 and 3 is confirmed.

Claim 1 is cancelled.

Claim 4 is determined to be patentable as amended.

New claims 5–28 are added and determined to be patentable.

4. The trocar assembly of claim [1] 2, wherein the assembly includes:
 (e) means for limiting the axial movement of the shield relative to the obturator to positions between the extended position and retracted position.

5. *A trocar assembly comprising:*
 *(a) an elongate trocar obturator having a piercing tip with three cutting edges at its front end;*
 *(b) an elongate trocar tube in which the trocar obturator is housed;*
 *(c) a tubular protective shield mounted concentrically around the trocar obturator and being axially movable relative to the trocar obturator between a normally extended position and a retracted position, the protective shield having a forward inwardly tapering outer surface, a cylindrical outer surface proximal of the forward inwardly tapering outer surface and three radially extending slots formed through the protective shield, each slot extending from the front end of the forward inwardly tapering outer surface to a point on the cylindrical outer surface, wherein each of the piercing tip cutting edges is aligned with a corresponding radially extending slot; and*
 *(d) biasing means acting on the rear end of the protective shield, whereby the shield is forced to said retracted position to expose the piercing tip when the trocar is being inserted through the wall of a body cavity and is biased by said means to said extended position to shield the piercing tip once the trocar has pierced the wall.*

6. *The trocar assembly of claim 5 wherein the assembly includes:*
 *(e) means for reversibly locking the shield in said extended position.*

7. *The trocar assembly of claim 6 wherein the means for reversibly locking the shield in said extended position is a manually operable slide valve that has a bore through which the obturator and shield extend, the bore has a radial locking tooth that is adapted to engage a slot in the wall of the shield, the valve being slidable transversely to the shield from a normally locked position in which the tooth is engaged in the slot to an unlocked position in which the tooth is disengaged, whereby the shield may be moved axially to said retracted position.*

8. *The trocar assembly of claim 5, wherein the assembly includes:*
 *(e) means for limiting the axial movement of the shield relative to the obturator to positions between the extended position and retracted position.*

9. *A trocar assembly comprising:*
 *(a) an elongate trocar obturator having a piercing tip with three cutting edges at its front end;*
 *(b) an elongate trocar tube in which the trocar obturator is housed;*
 *(c) a tubular protective shield mounted concentrically around the trocar obturator and being axially movable relative to the trocar obturator between a normally extended position and a retracted position, the protective shield having proximal and distal ends with three radially extending slots formed through the protective shield at the distal end, wherein each of the piercing tip cutting edges is aligned with a corresponding radially extending slot; and*
 *(d) biasing means acting on the rear end of the protective shield, whereby the shield is formed to said retracted position to expose the piercing tip when the trocar is being inserted through the wall of a body cavity and is biased by said means to said extended position to shield the piercing tip once the trocar has pierced the wall.*

10. *The trocar assembly of claim 9 wherein the assembly includes:*
 *(e) means for reversibly locking the shield in said extended position.*

11. *The trocar assembly of claim 10 wherein the means for reversibly locking the shield in said extended position is a manually operable slide valve that has a bore through which the obturator and shield extend, the bore has a radial locking tooth that is adapted to engage a slot in the wall of the shield, the valve being slidable transversely to the shield from a normally locked position in which the tooth is engaged in the slot to an unlocked position in which the tooth is disengaged, whereby the shield may be moved axially to said retracted position.*

12. *The trocar assembly of claim 9, wherein the assembly includes:*
 *(e) means for limiting the axial movement of the shield relative to the obturator to positions between the extended position and retracted position.*

13. *The trocar assembly of claim 9, wherein the protective shield distal end has an inwardly tapering outer surface and a cylindrical outer surface proximal of the inwardly tapering outer surface.*

14. *The trocar assembly of claim 13, wherein each radial slot extends from the distal end of the inwardly tapering outer surface to a point on the cylindrical outer surface.*

15. *A trocar assembly comprising:*
 *(a) an elongate trocar obturator having a piercing tip with three cutting edges at its front end;*
 *(b) an elongate trocar tube in which the trocar obturator is housed;*
 *(c) a tubular protective shield mounted concentrically around the trocar obturator and being axially movable relative to the trocar obturator between a normally extended position and a retracted position, the protective shield having a forward inwardly tapering outer surface, a cylindrical outer surface proximal of the forward inwardly tapering outer surface and three radially extending slots formed through the protective shield, each slot extending from the front end of the* forward inwardly tapering outer surface to a point on the cylindrical outer surface, wherein each of the piercing tip cutting edges is aligned with a corresponding radially extending slot; and (d) a spring action on the rear end of the protective shield, whereby the shield is forced to said retracted position to expose the piercing tip when the trocar is being inserted through the wall of a body cavity and is biased by said spring to said extended position to shield the piercing tip once the trocar has pierced the wall.

16. The trocar assembly of claim 15 wherein the assembly includes:

(e) means for reversibly locking the shield in said extended position.

17. The trocar assembly of claim 16 further comprising a manually operable slide valve with a radial locking tooth adapted to engage the shield, the valve being slidable transversely to the shield from a normally locked position, in which the tooth is engaged with the shield, to an unlocked position, in which the tooth is disengaged from the shield and the shield may be moved axially to said retracted position.

18. The trocar assembly of claim 15, wherein the assembly includes:

(e) means for limiting the axial movement of the shield relative to the obturator to positions between the extended and retracted position.

19. A trocar assembly comprising:

(a) an elongate trocar obturator having a piercing tip at its front end;

(b) an elongate trocar tube in which the trocar obturator is housed;

(c) a tubular protective shield mounted concentrically around the trocar obturator and being axially movable relative to the trocar obturator between a normally extended position and a retracted position;

(d) biasing means acting on the rear end of the protective shield, whereby the shield is forced to said retracted position to expose the piercing tip when the trocar is being inserted through the wall of a body cavity and is biased by said means to said extended position to shield the piercing tip once the trocar has pierced the wall; and (e) a locking member movable between a first position, wherein the shield is free to move in an axial direction relative to the obturator, and a second position, wherein the locking member engages a portion of the shield and the shield is prevented from moving in an axial direction relative to the obturator.

20. The trocar assembly of claim 19, wherein the locking member is a tooth adapted to engage a slot formed in the shield.

21. The trocar assembly of claim 19, wherein the shield covers the piercing tip of the obturator when the locking member is in the second position.

22. A trocar assembly comprising:

(a) an elongate trocar obturator having a piercing tip at its front end;

(b) an elongate trocar tube subassembly having a first grip that receives a trocar tube in which the trocar obturator is housed;

(c) a tubular protective shield mounted concentrically around the trocar obturator and being axially movable relative to the trocar obturator between a normally extended position and a retracted position;

(d) biasing means acting on the rear end of the protective shield, whereby the shield is forced to said retracted position to expose the piercing tip when the trocar is being inserted through the wall of a body cavity and is biased by said means to said extended position to shield the piercing tip once the trocar has pierced the wall; and (e) a second grip, wherein the obturator, protective shield and biasing means are at least partially disposed within the second grip, and wherein the second grip, obturator, protective shield and biasing means together define a trocar subassembly that is separable from the trocar tube subassembly.

23. The trocar assembly of claim 22, wherein the biasing means acting on the rear end of the protective shield is a spring.

24. The trocar assembly of claim 22, wherein the first grip and the second grip are interfitting but separable from each other.

25. The trocar assembly of claim 24, wherein said first and second grips are configured to snugly interfit.

26. The trocar assembly of claim 25, wherein the trocar tube subassembly further comprises a slide valve assembly received within said first grip.

27. The trocar assembly of claim 22, further comprising means for locking said obturator and protective shield in the second grip.

28. The trocar assembly of claim 27, wherein said protective shield includes a slot and said locking means includes a post which extends through said slot.

* * * * *